United States Patent
Sugimoto et al.

(10) Patent No.: US 11,298,340 B2
(45) Date of Patent: Apr. 12, 2022

(54) PHARMACEUTICAL COMPOSITION

(71) Applicant: KOWA COMPANY, LTD., Nagoya (JP)

(72) Inventors: Shin Sugimoto, Fuji (JP); Akito Minamizono, Fuji (JP)

(73) Assignee: KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 16/627,178

(22) PCT Filed: Jun. 29, 2018

(86) PCT No.: PCT/JP2018/024887
§ 371 (c)(1),
(2) Date: Dec. 27, 2019

(87) PCT Pub. No.: WO2019/004452
PCT Pub. Date: Jan. 3, 2019

(65) Prior Publication Data
US 2020/0121650 A1  Apr. 23, 2020

(30) Foreign Application Priority Data
Jun. 30, 2017 (JP) .............................. JP2017-129306

(51) Int. Cl.
*A61K 31/423* (2006.01)

(52) U.S. Cl.
CPC .................................. *A61K 31/423* (2013.01)

(58) Field of Classification Search
CPC .................................................... C07D 31/423
See application file for complete search history.

(56) References Cited

U.S. PATENT DOCUMENTS

| 7,109,226 B2 * | 9/2006 | Yamazaki | ................. A61P 3/10 514/375 |
|---|---|---|---|
| 2005/0101636 A1 | 5/2005 | Yamazaki et al. | |
| 2015/0164809 A1 | 6/2015 | Nishida | |
| 2015/0196538 A1 | 7/2015 | Takizawa et al. | |
| 2016/0136138 A1 | 5/2016 | Shibata et al. | |

FOREIGN PATENT DOCUMENTS

| JP | 2015-515498 A | 5/2015 | |
|---|---|---|---|
| WO | WO 2005/023777 A1 | 3/2005 | |
| WO | WO 2014/024268 A1 | 2/2014 | |
| WO | WO 2014/050134 A1 | 4/2014 | |
| WO | WO 2014/051023 A1 | 4/2014 | |
| WO | WO 2014/065427 A1 | 5/2014 | |
| WO | WO-2014065427 A1 * | 5/2014 | ........... A61K 31/519 |
| WO | WO 2015/005365 A1 | 1/2015 | |

OTHER PUBLICATIONS

Japanese Office Action dated Mar. 30, 2021 in Japanese Patent Application No. 2019-527075 (with English translation), 6 pages.
Wakiyama Naoki, "Stability and Shelf Life of Pharmaceuticals" Materials Life, vol. 3, No. 2, Apr. 1991, pp. 104-109 (with partial English Machine translation).
Yukiyoshi Yamazaki, et al., "A practical Synthesis of the PPARα Agonist, (R)-K-13675, Starting from (S)-2-Hydroxybutyrolactone" Tetrahedron, vol. 64, No. 35, 2008, pp. 8155-8158.
International Search Report dated Aug. 21, 2018 in PCT/JP2018/024887 filed Jun. 29, 2018, 2 pages.
Jean-Charles Fruchart, "Selective peroxisome proliferator-activated receptora modulators (SPPARMα): The next generation of peroxisome proliferator-activated receptor α-agonists," Cardiovascular Diabetology, vol. 12, No. 82, 2013, pp. 1-8.
Nathalie Hennuyer, et al., "The novel selective PPARα modulator (SPPARMα) pemafibrate improves dyslipidemia, enhances reverse cholesterol transport and decreases inflammation and atherosclerosis," Atherosclerosis, vol. 249, 2016, pp. 200-208.
"Report on the deliberation results of parmodia tablets 0.1 mg," Pharmaceutical Evaluation Division of Pharmaceutical Safety and Environmental Health Bureau, Ministry of Health, Labour and Welfare, Jul. 3, 2017, 84 Pages (with partial English language translation).
Yukiyoshi Yamazaki, et al., "Enantioselective Synthesis of the PPARα Agonist (R)-K-13675 via (S)-2-Hydroxybutyrolactone," Synthesis, No. 7, 2008, pp. 1017-1022.

* cited by examiner

*Primary Examiner* — Kamal A Saeed
(74) *Attorney, Agent, or Firm* — Oblon, McClelland, Maier & Neustadt, L.L.P.

(57) ABSTRACT

Provided is a pharmaceutical composition which contains pemafibrate, a salt thereof or a solvate thereof and has excellent stability. A pharmaceutical composition is provided containing pemafibrate, a salt thereof or a solvate thereof and having a moisture content of 2.4 mass % or less.

21 Claims, 1 Drawing Sheet

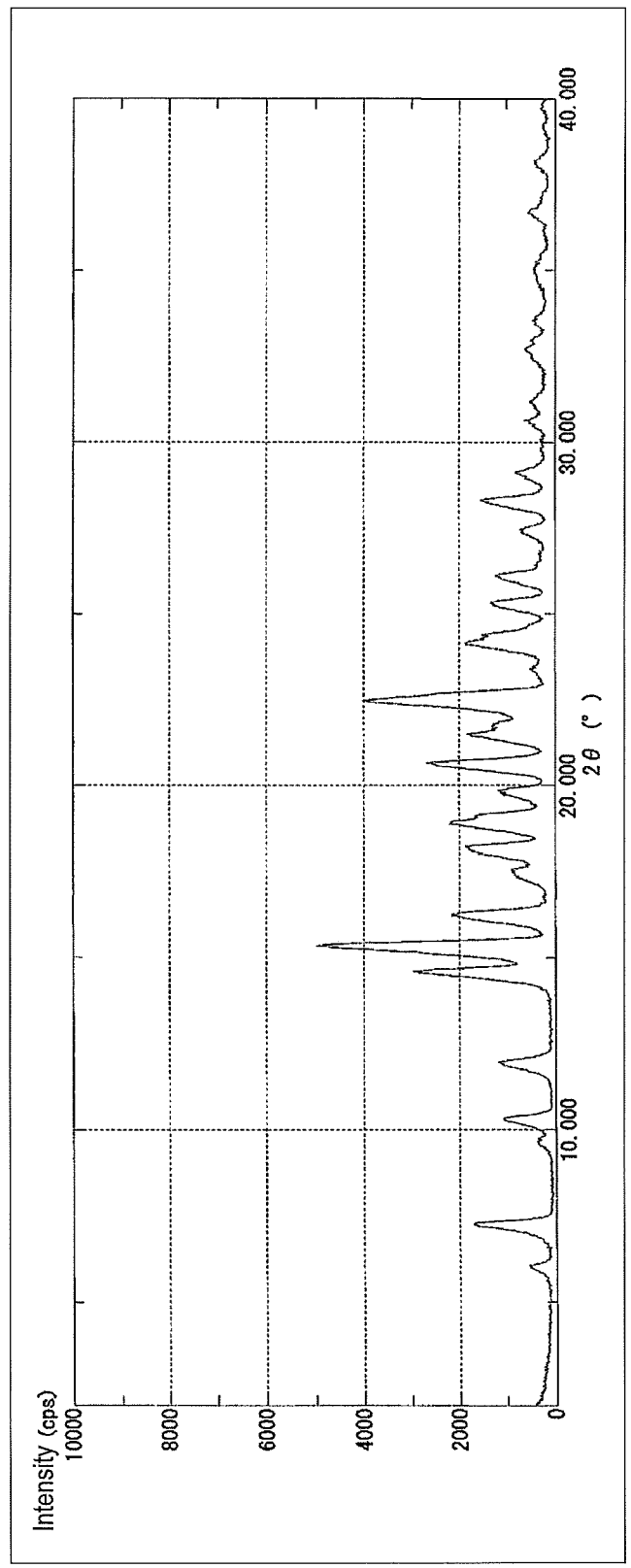

PHARMACEUTICAL COMPOSITION

FIELD OF THE INVENTION

The present invention relates to a pharmaceutical composition etc.

BACKGROUND OF THE INVENTION

It is known that pemafibrate (Chemical Name: (2R)-2-[3-([1,3-Benzoxazol-2-yl[3-(4-methoxyphenoxy)propyl]amino]methyl)phenoxy]butanoic acid) (International Nonproprietary Name: pemafibrate) represented by the following structural formula:

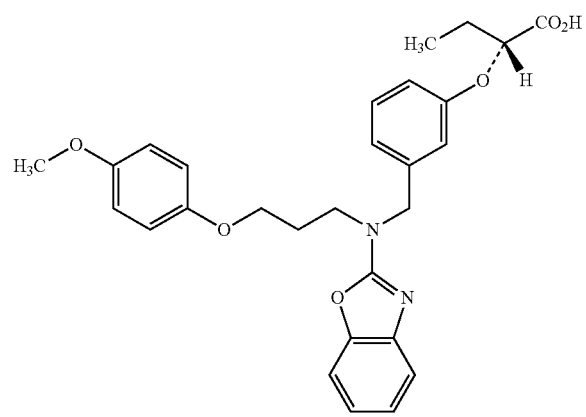

a salt thereof or a solvate thereof has excellent PPAR-α agonist activity, exhibits plasma triglyceride concentration reducing action, HDL cholesterol increasing action, etc., and is useful for prevention and treatment of dyslipidemia (hyperlipidemia) (Patent Document 1 and Non-Patent Documents 1 and 2), and useful for prevention and treatment of NAFLD (non-alcoholic fatty liver disease) (Patent Document 2).

Meanwhile, a compound useful as an active component for a pharmaceutical preparation is normally formulated as some pharmaceutical composition, and administered, and it is not unusual that a long time passes until a pharmaceutical composition is administered after production of the pharmaceutical composition. Thus, from the viewpoint of exhibiting expected drug efficacy and avoiding unanticipated adverse side effects, it is very important to secure stability of active components in the pharmaceutical composition.

PRIOR ART DOCUMENTS

Patent Documents

Patent Document 1: International Publication No. WO2005/023777
Patent Document 2: International Publication No. WO2015/005365

Non-Patent Documents

Non-Patent Document 1: Yukiyoshi Yamazaki, et al., Synthesis, 2008(7), 1017-1022.
Non-Patent Document 2: Fruchart J C., Cardiovasc Diabetol., 2013; 12: 82.

SUMMARY OF THE INVENTION

Problems to be Solved by the Invention

However, stability of active components significantly depends on the physical and chemical properties of components, but it is often impossible to predict such properties from the chemical structures of the components, and there are not a few cases where a problem becomes evident only when a pharmaceutical composition is actually produced. Thus, establishment of a technique for securing stability of active components in a pharmaceutical composition commonly requires considerable try and error.

Pemafibrate, a salt thereof or a solvate thereof has been only reported to exhibit the above-described pharmacological effects, and has heretofore not been specifically studied in terms of a pharmaceutical composition, and stability in a pharmaceutical composition has heretofore not been reported at all.

In these circumstances, for providing a pemafibrate-containing pharmaceutical composition having excellent stability, the present inventors have extensively conducted studies, and found that when a pemafibrate-containing pharmaceutical composition has a moisture content of larger than 3 mass %, the amount of decomposition products (related substances) of pemafibrate increased, though pemafibrate itself is highly stable to moisture content, leading to development of problems with stability.

Thus, an object of the present invention is to provide a pharmaceutical composition which contains pemafibrate, a salt thereof or a solvate thereof and has excellent stability.

Means for Solving the Problems

In view of the above, the present inventors have further extensively conducted studies of stability of pemafibrate in a pharmaceutical composition, and found that there is a correlation between the stability of pemafibrate and the moisture content of a pharmaceutical composition and that, by setting the moisture content of the pharmaceutical composition to 2.4 mass % or less, the increase of decomposition products of pemafibrate is so suppressed as to enable a pemafibrate-containing pharmaceutical composition to obtain an excellent stability. The present invention has been accomplished on the basis of this finding.

Accordingly, the present invention provides a pharmaceutical composition comprising pemafibrate, a salt thereof or a solvate thereof and having a moisture content of 2.4 mass % or less.

The present invention also provides a method for stabilizing pemafibrate, a salt thereof or a solvate thereof in a pharmaceutical composition, the method comprising the step of setting a moisture content in a pharmaceutical composition comprising pemafibrate, a salt thereof or a solvate thereof to 2.4 mass % or less.

Effects of the Invention

According to the present invention, it is possible to provide a pemafibrate-containing pharmaceutical composition in which increase in the amount of decomposition products of pemafibrate is suppressed and thereby good stability is obtained.

BRIEF DESCRIPTION OF DRAWING

FIG. 1 shows a powder X-ray diffraction pattern of a pemafibrate crystal obtained in Test Example 3.

DETAILED DESCRIPTION OF THE INVENTION

<Pemafibrate, Salt thereof or Solvate thereof>

Herein, "pemafibrate, a salt thereof or a solvate thereof" includes pemafibrate (Chemical Name: (2R)-2-[3-([1,3-Benzoxazol-2-yl[3-(4-methoxyphenoxy)propyl]amino]methyl)phenoxy]butanoic acid) (International Nonproprietary Name: pemafibrate) itself, a pharmaceutically acceptable salt of pemafibrate and a solvate of pemafibrate or a pharmaceutically acceptable salt thereof with water, alcohol (for example ethanol) or the like. The pharmaceutically acceptable salt is not particularly limited, and examples thereof include acid addition salts and base addition salts. Specific examples of the acid addition salts include acid addition salts with inorganic acids, such as hydrochlorides, hydrobromides, hydroiodides, sulfate salts, nitrate salts and phosphate salts; and acid addition salts with organic acids, such as benzoate salts, methanesulfonate salts, ethanesulfonate salts, benzenesulfonate salts, p-toluenesulfonate salts, maleate salts, fumarate salts, tartrate salts, citrate salts and acetate salts. Specific examples of the base addition salts include metal salts such as sodium salts, potassium salts, lithium salts, calcium salts and magnesium salts; salts with amines such as ammonia, trimethylamine, triethylamine, pyridine, collidine and lutidine; and base addition salts with organic bases such as lysine, arginine, cinchonine and cinchonidine.

Pemafibrate, a salt thereof or a solvate thereof is a known compound, and can be produced through a method as disclosed in Patent Document 1, Non-Patent Document 1 or U.S. Pat. No. 7,109,226, for example. In the present invention, a pemafibrate crystal which can be produced through the method described in Non-Patent Document 1 (preferably a crystal showing a melting point of 95 to 101° C., particularly preferably 97 to 100° C. in measurement performed in accordance with The Japanese Pharmacopoeia, 17th Edition, Melting Point Determination Method 1) is preferably used. As is apparent from Test Examples below, a pemafibrate crystal produced through the method described in Non-Patent Document 1 is not hygroscopic, and therefore a pharmaceutical composition containing the same is readily adjusted in terms of moisture content at the time of production and has such an advantage as to able to suppress the change of moisture content during storage. The disclosures of the documents are incorporated herein by reference.

The content of pemafibrate, a salt thereof or a solvate thereof in the pharmaceutical composition is not particularly limited, and can be determined in appropriate consideration of the type of preparation, the sex, age and symptoms of a patient in need of the composition, and the like. For example, the content can be set so that the daily dose of pemafibrate, a salt thereof or a solvate thereof may be 0.05 to 0.8 mg, more preferably 0.075 to 0.6 mg, particularly preferably 0.1 to 0.4 mg, in terms of a free form of pemafibrate.

The content of pemafibrate, a salt thereof or a solvate thereof in the pharmaceutical composition is preferably 0.005 to 5 mass %, more preferably 0.01 to 1 mass %, particularly preferably 0.05 to 0.5 mass %, in terms of a free form of pemafibrate, with respect to the total mass of the pharmaceutical composition.

Herein, the dosage form of the "pharmaceutical composition" is not particularly limited, may be a solid, semisolid or liquid preparation, and can be selected according to the use purpose of the pharmaceutical composition. Examples of the dosage form of the pharmaceutical composition include dosage forms described in The Japanese Pharmacopoeia, 17th Edition, General Rules for Preparations. Specific examples of the peroral dosage form include solid preparations such as tablets (e.g. normal tablets, orally disintegrating tablets, chewable tablets, effervescent tablets, dispersion tablets and soluble tablets), capsules, granules (e.g. effervescent granules), powders and pills; semisolid preparations such as peroral jellies; liquid preparations such as peroral liquids (e.g. elixirs, suspensions, emulsions and lemonades). Examples of the parenteral dosage form include injections, inhalations, eye drops, ear drops, nasal drops, suppositories, solid external preparations, liquid external preparations, sprays, ointments, creams, gels and patches.

The pharmaceutical composition is preferably a solid preparation from the viewpoint of ease of administration and ease of production.

The solid preparation is preferably a peroral solid preparation, more preferably a tablet, a capsule, a granule, a powder or a pill, particularly preferably a tablet.

The moisture content of the pharmaceutical composition is necessarily 2.4 mass % or less from the viewpoint of suppressing increase in the amount of decomposition products of pemafibrate, preferably about 2.1 mass % or less, more preferably about 1.9 mass % or less, yet more preferably about 1.7 mass % or less, yet more preferably about 1.5 mass % or less, particularly preferably about 1.3 mass % or less; and preferably about 0.3 mass % or more, more preferably about 0.5 mass % or more, still more preferably about 0.8 mass % or more, yet more preferably about 1.0 mass % or more, particularly preferably about 1.2 mass % or more. Particularly when the moisture content of the pharmaceutical composition is from about 0.8 to about 1.5 mass % (further particularly from about 1.2 to about 1.3 mass %), increase in the amount of decomposition products of pemafibrate is remarkably suppressed.

Here, the "moisture content of pharmaceutical composition" is measured through a loss-on-drying test method. Specifically, the moisture content is measured in terms of a loss-on-drying value (mass %) in accordance with The Japanese Pharmacopoeia, 17th Edition, Loss-on-Drying Test Method. Here, measurement conditions (drying temperature and drying time) are set as described below. When heat is applied, the drying temperature may be set so that the amount of held water can be measured depending on components blended in the pharmaceutical composition. For example, when an additive for pharmaceutical preparation having crystal water is blended, a temperature low enough to prevent evaporation of the crystal water is set. Specifically, such a temperature may be, for example, about 60 to 80° C. when the pharmaceutical composition is dried at normal pressure. The drying time is set to time with which a roughly constant moisture content may be attained. Specifically, the drying time is set to, for example, time with which the amount of change in measured loss-on-drying value per hour decreases to 0.1 mass % or less.

When the moisture content of a pharmaceutical composition packed in a tight package is measured, it is preferable to measure the moisture content immediately after taking out the pharmaceutical composition from the tight package from the viewpoint of accurately evaluating the moisture content in the tight package.

In addition to the above-described components, pharmaceutically acceptable carriers (additives for pharmaceutical preparation) may be added to the pharmaceutical composition of the present invention depending on its dosage form. Examples of the additives for pharmaceutical preparation include, but are not limited to, diluents, disintegrants, binders, lubricants, plasticizers, film formers, powders, poorly water-soluble polymer substances, antioxidants, flavors and sweetening agents. As specific examples of these additives for pharmaceutical preparation, those described in Japanese Pharmaceutical Excipients Directory 2016 (issued by Yakuji Nippo, Limited), Handbook of Pharmaceutical Excipients, Seventh Edition (issued by Pharmaceutical Press), etc. may be used.

Specific examples of the diluents include inorganic diluents such as aluminum silicate, anhydrous sodium sulfate, anhydrous dibasic calcium phosphate, sodium chloride, calcium silicate, light anhydrous silicic acid, heavy anhydrous silicic acid, calcium sulfate, calcium monohydrogen phosphate, dibasic calcium phosphate, dibasic sodium phosphate, monobasic potassium phosphate, monobasic calcium phosphate and monobasic sodium phosphate; and organic diluents such as corn syrup solids, starch (wheat starch, rice starch, corn starch, partially pregelatinized starch, etc.), fructose, caramel, agar, xylitol, paraffin, microcrystalline cellulose, sucrose, maltose, lactose, lactose monohydrate, white soft sugar, glucose, pullulan, polyoxyethylene hydrogenated castor oil, maltitol, reduced maltose starch syrup, powdery reduced maltose starch syrup, erythritol, sorbitol, mannitol, lactitol, trehalose, reduced palatinose, aminoalkyl methacrylate copolymer E, polyvinylacetal diethylaminoacetate and calcium citrate. These diluents may be used singly, or in combinations of two or more thereof.

Among these diluents, light anhydrous silicic acid, microcrystalline cellulose, lactose monohydrate and mannitol are preferable.

Specific examples of the disintegrants include superdisintegrants such as carboxymethyl starch sodium, croscarmellose sodium and crospovidone, carmellose, carmellose calcium, starch, sucrose fatty acid ester, gelatin, sodium hydrogen carbonate, dextrin, dehydroacetic acid and salts thereof, povidone and polyoxyethylene hydrogenated castor oil 60. These disintegrants may be used singly, or in combinations of two or more thereof.

Among these disintegrants, carboxymethyl starch sodium, croscarmellose sodium and crospovidone are preferable.

Specific examples of the binders include oils and fats such as tallow hydrogenated oil, hydrogenated oil, hydrogenated vegetable oil, soybean hydrogenated oil, carnauba wax, white beeswax, yellow beeswax and Japan wax, methylcellulose, hydroxypropylcellulose, hypromellose, carmellose sodium, starch (wheat starch, rice starch, corn starch, partially pregelatinized starch, etc.), dextrin, pullulan, acacia, agar, gelatin, tragacanth, sodium alginate, povidone, polyvinyl alcohol, aminoalkyl methacrylate copolymer E and polyvinylacetal diethylaminoacetate. These binders may be used singly, or in combinations of two or more thereof.

Among these binders, carnauba wax, hydroxypropylcellulose, hypromellose, carmellose sodium and starch (wheat starch, rice starch, cornstarch, partially pregelatinized starch, etc.) are preferable.

Specific examples of the lubricants include calcium stearate, magnesium stearate, sodium stearyl fumarate and sucrose fatty acid ester. Theses lubricants may be used singly, or in combinations of two or more thereof.

Among these lubricants, calcium stearate, magnesium stearate and sodium stearyl fumarate are preferable.

Specific examples of the plasticizers include triethyl citrate, glycerin, sesame oil, sorbitol, castor oil and polysorbate 80 (polyoxyethylene(20)sorbitan oleate). These plasticizers may be used singly, or in combinations of two or more thereof.

Among these plasticizers, triethyl citrate and glycerin are preferable.

Specific examples of the film formers include alkylcelluloses such as methylcellulose and ethylcellulose; alginic acid or salts thereof such as sodium alginate; carrageenan; carboxyalkylcelluloses such as carboxymethylcellulose sodium, carboxymethylcellulose calcium, carboxymethylcellulose potassium, carboxymethylcellulose and carboxymethylethylcellulose; xanthan gum; hydroxyalkylcelluloses such as hydroxymethylcellulose, hydroxyethylcellulose, hydroxypropylcellulose, hypromellose (hydroxypropylmethylcellulose); hydroxyalkylcellulose phthalate such as hydroxypropylmethylcellulose phthalate; pullulan; polyvinyl acetate; polyvinyl acetate phthalate; and polyvinylpyrrolidone. These film formers may be used singly, or in combinations of two or more thereof.

Among these film formers, hydroxyalkylcelluloses are preferable.

Specific examples of the powders include organic and inorganic powders such as powders of talc, titanium oxide, yellow ferric oxide, red ferric oxide and legal color pigments. These powders may be used singly, or in combinations of two or more thereof.

Among these powders, titanium oxide, red ferric oxide and legal color pigments are preferable.

Specific examples of the poorly water-soluble polymer substances include carboxyvinyl polymers and aminoalkyl methacrylate copolymers. These substances may be used singly, or in combinations of two or more thereof.

Specific examples of the antioxidants include ascorbic acid, sodium hydrogen sulfite, sodium sulfite, sodium edetate, erythorbic acid, tocopherol acetate, dibutylhydroxytoluene, natural vitamin E, tocopherol and butylhydroxyanisole. These antioxidants may be used singly, or in combinations of two or more thereof.

Specific examples of the flavors include terpenes such as limonene, pinene, camphene, cymene, cineole, citronellol, geraniol, nerol, linalool, menthol, terpineol, rhodinol, borneol, isoborneol, menthone, camphor, eugenol and cinnzeylanol; terpene-containing essential oils such as bitter orange oil, orange oil, peppermint oil, camphor white oil, eucalyptus oil, turpentine oil, lemon oil, ginger oil, clove oil, cinnamon oil, lavender oil, fennel oil, chamomile oil, fermented soybean oil and spearmint oil; and acidifiers such as ascorbic acid, tartaric acid, citric acid, malic acid and salts thereof. These flavors may be used singly, or in combinations of two or more thereof.

Examples of the sweetening agents include aspartame, stevia, sucralose, glycyrrhizic acid, thaumatin, acesulfame potassium, saccharin and saccharin sodium, and these sweetening agents may be used singly, or in combinations of two or more thereof.

The pharmaceutical composition of the present invention can be produced through a known method depending on its dosage form.

For example, the pharmaceutical composition, when it is a solid preparation, can be produced through appropriate combination of unit operations such as grinding, mixing, granulation, drying, grain size adjustment, classification, filling, pelletizing and coating.

More specifically, for example, when the dosage form of the pharmaceutical composition is a granular preparation such as a granule, a powder or a pill, additives for pharmaceutical preparation such as diluents, binders, disintegrants and lubricants are used, and after mixing these components in accordance with needs, the mixture is granulated through a known granulation method such as extrusion granulation, tumbling granulation, agitation granulation, fluidized bed granulation, spray granulation, melt granulation or crushing granulation to obtain a granulated product, and the granulated product is subjected to classification, grain size adjustment and the like in accordance with needs, whereby the pharmaceutical composition can be produced. The obtained granulated product can be coated through a known method with a coating agent etc.

When the dosage form of the pharmaceutical composition is a tablet, appropriate additives for pharmaceutical preparation such as diluents, binders, disintegrants and lubricants are used in accordance with needs, and these components are mixed to obtain the mixture, which is then directly compressed (pelletized) (through a direct powder compression method), or compressed (pelletized) (through a semidry grain compression method, dry granule compression method, wet grain compression method or the like) after the aforementioned granulated product is subjected to classification, grain size adjustment and the like, whereby the pharmaceutical composition can be produced. The obtained compressed product (tablet) can be coated through a known method with a coating agent etc.

When the dosage form of the pharmaceutical composition is a capsule, the granulated product or compressed product may be capsulated.

Examples of the means for adjusting the moisture content of the pharmaceutical composition include humidification means and drying means, and theses means may be appropriately selected and combined depending on the dosage form of the pharmaceutical composition, etc.

Examples of the humidification means include means using a hydrous solvent as a kneading liquid in wet granulation operation.

Examples of the drying means include means using a drier and means using a desiccant. Here, as the drier, one that is commonly used in the fields of pharmaceutical preparations and food products can be used, and specific examples thereof include compartment driers, fluidized bed driers, spray driers, freeze driers, vacuum driers and high-frequency driers. As the desiccant, one that commonly used in the fields of pharmaceutical preparations and food products can be used, and a specific example thereof is one or more selected from the group consisting of silica gel, silica alumina gel (e.g. allophane), natural zeolite, synthetic zeolite (e.g. molecular sieve), quicklime (calcium oxide), bentonite clay (e.g. montmorillonite), calcium chloride, magnesium chloride and magnesium oxide, and a mixture of these desiccants with activated carbon may be used. As the drying means, a method using a drier is preferable from the viewpoint of ease of adjusting the moisture content of the pharmaceutical composition.

The humidification means or drying means may be carried out during or after production of the pharmaceutical composition.

The pharmaceutical composition may further be stored in a tight package (hereinafter, a pharmaceutical composition stored in a tight package is referred herein to as a "pharmaceutical preparation"). By storing a pharmaceutical composition in a tight package, entry of moisture from outside the package is prevented, with which the moisture content in the pharmaceutical composition stored inside the package is stably maintained over a long period of time. As a result of this, increase in the amount of decomposition products of pemafibrate in the pharmaceutical composition can be suppressed over a long period of time.

Herein, the "tight package" means a package capable of suppressing substantive entry of moisture from outside the package in a state of normal handling, transportation, storage or the like, and includes the "tight container" and the "hermetic container" defined in The Japanese Pharmacopoeia, 17th Edition, General Rules. The tight package may be either shaped or unshaped, and specific examples of the tight package include bottle packages, strip packages (SP), press through packages (PTP), pillow packages and stick packages. The tight package may be a combination of two or more of these packages, and as a specific example, the pharmaceutical composition is first packed in a PTP package, and the PTP package is then packed in a pillow package.

The packaging material (raw material) for the tight package is not particularly limited as long as it can exhibit a moisture-proof property, and it is possible to appropriately use a material which is used for moisture-proofing of contents susceptible to moisture, etc. in the fields of pharmaceutical preparations, food products and the like.

Examples of the material for the bottle body used for bottle packages include glass, plastics (polyester, polyethylene (including low-density polyethylene (LDPE), medium-density polyethylene (MDPE) and high-density polyethylene (HDPE)), polycarbonate, polystyrene, polypropylene, etc.), and metals (aluminum etc.). In preparation of a bottle package, for example, an appropriate amount of the pharmaceutical composition may be stored in a commercially available bottle, followed by sealing the bottle with an appropriate cap or lid. As the bottle, one having a size suited for the amount etc. of the pharmaceutical composition to be stored may be appropriately selected, and the capacity of the bottle is, for example, about 10 to 500 mL, preferably 14 to 400 mL, more preferably 24 to 350 mL. The material for the bottle package is preferably polyethylene or polypropylene, more preferably low-density polyethylene (LDPE) or high-density polyethylene (HDPE), particularly preferably high-density polyethylene (HDPE).

Examples of the packaging materials to be used for SP packages, PTP packages, pillow packages and stick packages include resins such as biaxially oriented polypropylene (OPP), biaxially oriented polyester (PET), glycol-modified PET (PET-G), biaxially oriented nylon (ONy, PA), cellophane, paper, low-density polyethylene (LDPE), linear low-density polyethylene (L-LDPE), ethylene-vinyl acetate copolymers (EVA), non-oriented polypropylene (CPP, IPP), ionomer resins (IO), ethylene-methacrylic acid copolymers (EMAA), polyacrylonitrile (PAN), biaxially oriented polyvinylidene chloride (PVDC), ethylene-vinyl alcohol copolymer resins (EVOH), polyvinyl chloride (PVC), cyclic polyolefins (COC), non-oriented nylon (CNy), polycarbonate (PC), polystyrene (PS) and rigid polyvinyl chloride (VSC); and metal foils such as aluminum foil (AL), and one or more of these materials may be appropriately combined to form a multilayer structure. Examples of the multilayer structure include laminates of PVC and PVDC (PVC/PVDC; hereinafter, structures are expressed in similar expressed forms), PVC/PVDC/PE/PVC, PVC/PVDC/PE/PVDC/PVC, CPP/COC/CPP, PVC/AL, CPP/AL and CPP/CPP/CPP. Examples of the method for forming such a multilayer structure include known lamination methods such as extrusion lamination, dry lamination, coextrusion lamination, thermal lamination, wet lamination, non-solvent lamination and heat lamination. As packaging materials to be used for SP packages, PTP packages, pillow packages and stick packages, polyvinyl chloride and aluminum foil are preferable.

As a form of the PTP package, one piece or one dosage unit of the pharmaceutical composition is stored in each of a desired number of pockets formed on a resin sheet etc. through a known method, and the pockets are then covered with a lid material which is a sheet formed of a metal foil such as aluminum foil. The PTP package may be a so-called PTP package with aluminum on both sides in which a sheet provided with pockets is also formed of aluminum foil. In the present invention, it is preferable to further pack the PTP package in a pillow package (e.g. aluminum pillow package) from the viewpoint of enhancing the moisture-proof property.

As a form of the SP package, pillow package or stick package, one piece or one dosage unit of the pharmaceutical composition is packed through a known method using a resin sheet, a sheet formed of aluminum foil, or the like. In the present invention, it is preferable to use a sheet formed of aluminum foil from the viewpoint of enhancing the moisture-proof property.

Herein, when the package is a bottle package, the occupancy (volume) of the pharmaceutical composition in the pharmaceutical preparation in the package is normally 25 to 90%, preferably 28 to 75%, more preferably 30 to 50%. When the package is an SP package, a PTP package, a pillow package or a stick package, the occupancy is normally 30 to 98%, preferably 40 to 95%, more preferably 45 to 93%, particularly preferably 50 to 90%. In this case, the occupancy means an occupancy of the pharmaceutical composition with respect to the total volume of the inside of the package, and in calculation of the space occupancy, a pad, inside plug or the like for preventing breakage of the pharmaceutical composition stored in the package is not considered.

As the tight package, a commercially available package may be used as it is, or a commercially available packaging material may be processed and used. Examples of the commercially available package for bottle packages include Z-Series (manufactured by Hanshin Kasei Kogyo Co., Ltd.). Examples of the packaging materials for SP packages, PTP packages, pillow packages and stick packages include SUMILITE VSS, SUMILITE VSL, SUMILITE NS and SUMILITE FCL (each manufactured by Sumitomo Bakelite Co., Ltd.), TAS Series (manufactured by Taisei Kako Co., Ltd.), PIP VINYFOIL and PTP SUPERFOIL (each manufactured by Mitsubishi Plastics, Inc.), NIPAK Aluminum Foil (manufactured by Nippon Foil Mgf. Co., Ltd.) and Aluminum Foil Silver Base (manufactured by Daiwa Chemical Industries Co., Ltd.).

The method for storing the pharmaceutical composition in the tight package is not particularly limited, and it is possible to arrange the pharmaceutical composition in the package through appropriate means for introducing the pharmaceutical composition into the package, etc. In this case, means for introducing a desiccant (e.g. columnar (tablet-shaped) or sheet-shaped desiccant) into the package together with the pharmaceutical composition may be used.

The disease to which the pharmaceutical composition of the present invention is applied is not limited, and the pharmaceutical composition can be widely used for prevention or treatment of diseases against which administration of pemafibrate is known or expected to be effective.

For example, pemafibrate, a salt thereof or a solvate thereof has excellent PPAR-α agonist activity, and exhibits plasma triglyceride concentration reducing action, HDL cholesterol increasing action, etc. Therefore, the pharmaceutical composition of the present invention can be used preferably as an agent for prevention and/or treatment of dyslipidemia (hyperlipidemia, more specifically, for example primary hyperlipidemia and secondary hyperlipidemia), further preferably as an agent for prevention and/or treatment of hypertriglyceridemia, etc.

In addition, pemafibrate, a salt thereof or a solvate thereof is useful for prevention or treatment of NAFLD (non-alcoholic fatty liver disease). Therefore, the pharmaceutical composition of the present invention can also be used as an agent for prevention and/or treatment of NAFLD (more preferably NASH (non-alcoholic steatohepatitis)), etc.

Further, pemafibrate, a salt thereof or a solvate thereof may be used as an agent for treatment of primary biliary cirrhosis, etc.

The administration route of the pharmaceutical composition is not particularly limited, and can be determined in appropriate consideration of the target disease, the type of preparation, the sex, age, symptoms of a patient in need of the composition, and the like, but peroral administration is preferable from the viewpoint of ease of administration. The daily dose of the pharmaceutical composition can be taken as a single dose, or can be divided into 2 to 4 daily administrations, and taken before each meal, between meals, after each meal, before bedtime, or the like.

For example, the following aspects are disclosed herein and should not be construed as limiting the present invention.

[1-1] A pharmaceutical composition comprising pemafibrate, a salt thereof or a solvate thereof and having a moisture content of 2.4 mass % or less (preferably 0.3 to 2.4 mass %, more preferably 0.5 to 2.4 mass %, still more preferably 0.8 to 2.4 mass %, yet more preferably 1.0 to 2.4 mass %, particularly preferably 1.2 to 2.4 mass %).

[1-2] The pharmaceutical composition according to [1-1], wherein the moisture content of the pharmaceutical composition is 2.1 mass % or less (preferably 0.3 to 2.1 mass %, more preferably 0.5 to 2.1 mass %, still more preferably 0.8 to 2.1 mass %, yet more preferably 1.0 to 2.1 mass %, particularly preferably 1.2 to 2.1 mass %).

[1-3] The pharmaceutical composition according to [1-1], wherein the moisture content of the pharmaceutical composition is 1.9 mass % or less (preferably 0.3 to 1.9 mass %, more preferably 0.5 to 1.9 mass %, still more preferably 0.8 to 1.9 mass %, yet more preferably 1.0 to 1.9 mass %, particularly preferably 1.2 to 1.9 mass %).

[1-4] The pharmaceutical composition according to [1-1], wherein the moisture content of the pharmaceutical composition is 1.7 mass % or less (preferably 0.3 to 1.7 mass %, more preferably 0.5 to 1.7 mass %, still more preferably 0.8 to 1.7 mass %, yet more preferably 1.0 to 1.7 mass %, particularly preferably 1.2 to 1.7 mass %).

[1-5] The pharmaceutical composition according to [1-1], wherein the moisture content of the pharmaceutical composition is 1.5 mass % or less (preferably 0.3 to 1.5 mass %, more preferably 0.5 to 1.5 mass %, still more preferably 0.8 to 1.5 mass %, yet more preferably 1.0 to 1.5 mass %, particularly preferably 1.2 to 1.5 mass %).

[1-6] The pharmaceutical composition according to [1-1], wherein the moisture content of the pharmaceutical composition is 1.3 mass % or less (preferably 0.3 to 1.3 mass %, more preferably 0.5 to 1.3 mass %, still more preferably 0.8 to 1.3 mass %, yet more preferably 1.0 to 1.3 mass %, particularly preferably 1.2 to 1.3 mass %).

[1-7] The pharmaceutical composition according to anyone of [1-1] to [1-6], wherein the pemafibrate, a salt thereof or a solvate thereof is a pemafibrate crystal.

[1-8] The pharmaceutical composition according to [1-7], wherein the pemafibrate crystal is a crystal having a melting point of 95 to 101° C. (preferably 97 to 100° C.).

[1-9] The pharmaceutical composition according to [1-7] or [1-8], wherein the pemafibrate crystal has a peak at one or more diffraction angles (2θ) selected from the group consisting of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

[1-10] The pharmaceutical composition according to [1-7] or [1-8], wherein the pemafibrate crystal has peaks at diffraction angles (2θ) of around 14.6±0.2°, around 15.3±0.2°, around 20.6±0.2° and around 22.5±0.2° in a powder X-ray diffraction pattern obtained by irradiation with Cu-Kα radiation.

[1-11] The pharmaceutical composition according to [1-7] or [1-8], wherein the pemafibrate crystal has peaks at diffraction angles (2θ) of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

[1-12] The pharmaceutical composition according to any one of [1-1] to [1-11], wherein the pharmaceutical composition is a solid preparation.

[1-13] The pharmaceutical composition according to any one of [1-1] to [1-12], wherein the pharmaceutical composition is a tablet, a capsule, a granule, a powder or a pill.

[1-14] The pharmaceutical composition according to any one of [1-1] to [1-13], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[1-15] A pharmaceutical preparation obtained by storing the pharmaceutical composition according to any one of [1-1] to [1-14] in a tight package.

[1-16] The pharmaceutical preparation according to [1-15], wherein the tight package is one or more selected from the group consisting of a bottle package, an SP package, a PTP package, a pillow package and a stick package.

[2-1] A method for stabilizing pemafibrate, a salt thereof or a solvate thereof in a pharmaceutical composition (preferably a method for suppressing increase in the amount of decomposition products of pemafibrate), the method comprising the step of setting a moisture content in a pharmaceutical composition comprising pemafibrate, a salt thereof or a solvate thereof to 2.4 mass % or less (preferably 0.3 to 2.4 mass %, more preferably 0.5 to 2.4 mass %, still more preferably 0.8 to 2.4 mass %, yet more preferably 1.0 to 2.4 mass %, particularly preferably 1.2 to 2.4 mass %).

[2-2] The method according to [2-1], wherein the moisture content of the pharmaceutical composition is set to 2.1 mass % or less (preferably 0.3 to 2.1 mass %, more preferably 0.5 to 2.1 mass %, still more preferably 0.8 to 2.1 mass %, yet more preferably 1.0 to 2.1 mass %, particularly preferably 1.2 to 2.1 mass %).

[2-3] The method according to [2-1], wherein the moisture content of the pharmaceutical composition is set to 1.9 mass % or less (preferably 0.3 to 1.9 mass %, more preferably 0.5 to 1.9 mass %, still more preferably 0.8 to 1.9 mass %, yet more preferably 1.0 to 1.9 mass %, particularly preferably 1.2 to 1.9 mass %).

[2-4] The method according to [2-1], wherein the moisture content of the pharmaceutical composition is set to 1.7 mass % or less (preferably 0.3 to 1.7 mass %, more preferably 0.5 to 1.7 mass %, still more preferably 0.8 to 1.7 mass %, yet more preferably 1.0 to 1.7 mass %, particularly preferably 1.2 to 1.7 mass %).

[2-5] The method according to [2-1], wherein the moisture content of the pharmaceutical composition is set to 1.5 mass % or less (preferably 0.3 to 1.5 mass %, more preferably 0.5 to 1.5 mass %, still more preferably 0.8 to 1.5 mass %, yet more preferably 1.0 to 1.5 mass %, particularly preferably 1.2 to 1.5 mass %).

[2-6] The method according to [2-1], wherein the moisture content of the pharmaceutical composition is set to 1.3 mass % or less (preferably 0.3 to 1.3 mass %, more preferably 0.5 to 1.3 mass %, still more preferably 0.8 to 1.3 mass %, yet more preferably 1.0 to 1.3 mass %, particularly preferably 1.2 to 1.3 mass %).

[2-7] The method according to any one of [2-1] to [2-6] wherein the pemafibrate, a salt thereof or a solvate thereof is a pemafibrate crystal.

[2-8] The method according to [2-7], wherein the pemafibrate crystal is a crystal having a melting point of 95 to 101° C. (preferably 97 to 100° C.).

[2-9] The method according to [2-7] or [2-8], wherein the pemafibrate crystal has a peak at one or more diffraction angles (2θ) selected from the group consisting of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

[2-10] The method according to [2-7] or [2-8], wherein the pemafibrate crystal has peaks at diffraction angles (2θ) of around 14.6±0.2°, around 15.3±0.2°, around 20.6±0.2° and around 22.5±0.2° in a powder X-ray diffraction pattern obtained by irradiation with Cu-Kα radiation.

[2-11] The method according to [2-7] or [2-8], wherein the pemafibrate crystal has peaks at diffraction angles (2θ) of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

[2-12] The method according to any one of [2-1] to [2-11], wherein the pharmaceutical composition is a solid preparation.

[2-13] The method according to any one of [2-1] to [2-12], wherein the pharmaceutical composition is a tablet, a capsule, a granule, a powder or a pill.

[2-14] The method according to any one of [2-1] to [2-13], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[2-15] The method according to any one of [2-1] to [2-14], further comprising the step of storing the pharmaceutical composition in a tight package.

[2-16] The method according to [2-15], wherein the tight package is one or more selected from the group consisting of a bottle package, an SP package, a PTP package, a pillow package and a stick package.

Moreover, the following aspects are also disclosed herein in addition to the above-mentioned aspects. As is apparent from Test Examples below, a pemafibrate crystal is not hygroscopic. Therefore, a pharmaceutical composition according to the following aspects is readily adjusted in terms of moisture content at the time of production and has such an advantage as to able to suppress the change of moisture content during storage.

[3-1] A pharmaceutical composition comprising a pemafibrate crystal.

[3-2] The pharmaceutical composition according to [3-1], wherein the pemafibrate crystal is a crystal having a melting point of 95 to 101° C. (preferably 97 to 100° C.).

[3-3] The pharmaceutical composition according to [3-1] or [3-2], wherein the pemafibrate crystal has a peak at one or more diffraction angles (2θ) selected from the group consisting of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

[3-4] The pharmaceutical composition according to [3-1] or [3-2], wherein the pemafibrate crystal has peaks at diffraction angles (2θ) of around 14.6±0.2°, around 15.3±0.2°, around 20.6±0.2° and around 22.5±0.2° in a powder X-ray diffraction pattern obtained by irradiation with Cu-Kα radiation.

[3-5] The pharmaceutical composition according to [3-1] or [3-2], wherein the pemafibrate crystal has peaks at diffraction angles (2θ) of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

[3-6] The pharmaceutical composition according to any one of [3-1] to [3-5], wherein the moisture content of the pharmaceutical composition is 2.4 mass % or less (preferably 0.3 to 2.4 mass %, more preferably 0.5 to 2.4 mass %, still more preferably 0.8 to 2.4 mass %, yet more preferably 1.0 to 2.4 mass %, particularly preferably 1.2 to 2.4 mass %).

[3-7] The pharmaceutical composition according to any one of [3-1] to [3-5], wherein the moisture content of the pharmaceutical composition is 2.1 mass % or less (preferably 0.3 to 2.1 mass %, more preferably 0.5 to 2.1 mass %, still more preferably 0.8 to 2.1 mass %, yet more preferably 1.0 to 2.1 mass %, particularly preferably 1.2 to 2.1 mass %).

[3-8] The pharmaceutical composition according to any one of [3-1] to [3-5], wherein the moisture content of the pharmaceutical composition is 1.9 mass % or less (preferably 0.3 to 1.9 mass %, more preferably 0.5 to 1.9 mass %, still more preferably 0.8 to 1.9 mass %, yet more preferably 1.0 to 1.9 mass %, particularly preferably 1.2 to 1.9 mass %).

[3-9] The pharmaceutical composition according to any one of [3-1] to [3-5], wherein the moisture content of the pharmaceutical composition is 1.7 mass % or less (preferably 0.3 to 1.7 mass %, more preferably 0.5 to 1.7 mass %, still more preferably 0.8 to 1.7 mass %, yet more preferably 1.0 to 1.7 mass %, particularly preferably 1.2 to 1.7 mass %).

[3-10] The pharmaceutical composition according to any one of [3-1] to [3-5], wherein the moisture content of the pharmaceutical composition is 1.5 mass % or less (preferably 0.3 to 1.5 mass %, more preferably 0.5 to 1.5 mass %, still more preferably 0.8 to 1.5 mass %, yet more preferably 1.0 to 1.5 mass %, particularly preferably 1.2 to 1.5 mass %).

[3-11] The pharmaceutical composition according to any one of [3-1] to [3-5], wherein the moisture content of the pharmaceutical composition is 1.3 mass % or less (preferably 0.3 to 1.3 mass %, more preferably 0.5 to 1.3 mass %, still more preferably 0.8 to 1.3 mass %, yet more preferably 1.0 to 1.3 mass %, particularly preferably 1.2 to 1.3 mass %).

[3-12] The pharmaceutical composition according to any one of [3-1] to [3-11], wherein the pharmaceutical composition is a solid preparation.

[3-13] The pharmaceutical composition according to any one of [3-1] to [3-12], wherein the pharmaceutical composition is a tablet, a capsule, a granule, a powder or a pill.

[3-14] The pharmaceutical composition according to any one of [3-1] to [3-13], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[3-15] A pharmaceutical preparation obtained by storing the pharmaceutical composition according to any one of [3-1] to [3-14] in a tight package.

[3-16] The pharmaceutical preparation according to [3-15], wherein the tight package is one or more selected from the group consisting of a bottle package, an SP package, a PTP package, a pillow package and a stick package.

The pemafibrate crystal can be produced by recrystallization from an ethyl acetate/heptane mixture in accordance with, for example, a method for producing a pemafibrate crystal as described in Non-Patent Document 1. Specifically, pemafibrate is added to ethyl acetate in an amount set so that the final concentration of the pemafibrate is about 20 w/v %, and the mixture is heated to about 60° C. to dissolve the pemafibrate, and allowed to cool. Thereafter, to the solution heptane about 2 to 5 times its volume is added, and the mixture is left standing at room temperature or so (1 to 30° C.) overnight or so to obtain a pemafibrate crystal.

EXAMPLES

The present invention will next be described in detail by way of Examples, which should not be construed as limiting the invention thereto.

In Test Examples below, measurement was performed through HPLC using an ODS column as a column and an ultraviolet spectrophotometer as a detector.

Test Example 1

Examination of Stability of Pemafibrate 250 mg of pemafibrate was placed in a dish, and stored in an uncapped state (open state) in a dark place at 40° C. and 75% relative humidity (RH) for 3 months.

The amounts of pemafibrate-derived decomposition products (related substances) before the start of storage and after storage at 40° C. and 75% RH for 3 months were evaluated through the following method.

The sum of related substance-derived peak areas was evaluated in terms of a ratio (%) to the pemafibrate-derived peak area using an HPLC apparatus, and the ratio was defined as the "Total amount (%) of related substances".

Table 1 shows the results.

TABLE 1

| | Total amount (%) of related substances | |
|---|---|---|
| | Before storage | After storage at 40° C. and 75% RH for 3 months |
| Pemafibrate alone stored in open state in dish | <0.05 | <0.05 |

As shown in Table 1, pemafibrate itself was stable against moisture content, and there was no substantive increase in the amount of related substances even after storage at a high humidity of 75% RH for 3 months.

Test Example 2

Stability Test

In accordance with the following method, a pharmaceutical composition (tablets) containing pemafibrate was produced, dried and thereby adjusted to have the moisture contents shown in Table 2 (the method for measuring the moisture content is as described below). Thereafter, the tablets, whose moisture contents had been adjusted, were packed in a glass bottle with a capacity of about 20 mL (tight container defined in The Japanese Pharmacopoeia, 17th Edition, General Rules) without gaps, and then stored in a dark place at 80° C. for 3 days. Subsequently, the total amounts (%) of pemafibrate-derived related substances before the start of storage and after storage at 80° C. for 3 days were evaluated using an HPLC apparatus through the same method as in Test Example 1, and then the increase (%) in the amount of the related substances was measured in accordance with the following method.

<Production of Tablets>

Pemafibrate, lactose monohydrate, croscarmellose sodium, hydroxypropylcellulose and microcrystalline cellulose were mixed together, then kneaded with purified water, granulated, dried, and then sized to obtain a granulated product. Magnesium stearate was mixed with the obtained granulated product, and the mixture was then compressed to obtain tablets containing 0.1 mg of pemafibrate in terms of a free form of pemafibrate per tablet (120 mg).

<Measurement of Moisture Content of Tablet>

The moisture content of the tablets was measured in terms of a loss-on-drying value in accordance with The Japanese Pharmacopoeia, 17th Edition, Loss-on-Drying Test Method. Specifically, some (nine) of the tablets after drying were taken out, ground to a diameter of 2 mm or less, placed in a weighing bottle, and spread so that the layers of the ground tablets had a thickness of 5 mm or less. Drying was then performed at normal pressure with a drying temperature of 80° C. and a drying time of 4 hours, and the loss-on-drying value was measured. 4 hours after the start of drying, the amount of change in loss-on-drying value per hour was 0.1 mass % or less, and thus it was determined that a constant moisture content was attained.

<Measurement of Increase (%) in the Amount of Related Substances>

From the total amounts (%) of pemafibrate-derived related substances before the start of storage and after storage at 80° C. for 3 days, an increase (%) in the amount of related substances was calculated in accordance with the following equation.

Increase (%) in the amount of related substances=
(total amount (%) of pemafibrate-derived related substances after storage at 80° C. for 3 days)−(total amount (%) of pemafibrate-derived related substances before start of storage).

Table 2 shows the results.

TABLE 2

| Moisture content (loss on-drying value) (mass %) | 0.8 | 1.2 | 1.3 | 1.5 | 2.4 | 3.4 |
|---|---|---|---|---|---|---|
| Increase (%) in the amount of related substances | 0.68 | 0.34 | 0.34 | 0.67 | 1.98 | 3.12 |

Table 2 reveals that there is a correlation between the moisture content of the pharmaceutical composition and the increase in the amount of related substances, and that the increase in the amount of decomposition products of pemafibrate is suppressed by setting the moisture content of the pharmaceutical composition to 2.4 mass % or less, while a large amount of decomposition products of pemafibrate is produced when the moisture content of the pharmaceutical composition is 3.4 mass %. Particularly in the case where the moisture content of the pharmaceutical composition is 0.8 to 1.5 mass %, increase in the amount of decomposition products of pemafibrate is significantly suppressed.

The above test results reveal that increase in the amount of related substances is suppressed by setting the moisture content of the pharmaceutical composition containing pemafibrate, a salt thereof or a solvate thereof to 2.4 mass % or less and therefore a pemafibrate-containing pharmaceutical composition excellent in stability can be obtained.

Test Example 3

Evaluation of Physical Properties of Pemafibrate Crystal

A pemafibrate crystal was produced by recrystallizing pemafibrate from an ethyl acetate/heptane mixture in accordance with the method for producing a pemafibrate crystal as described in Non-Patent Document 1.

For the obtained crystal, powder X-ray diffraction measurement, melting point measurement and hygroscopic property evaluation were performed in the following manner.

<Powder X-ray Diffraction Measurement>

The powder X-ray diffraction measurement was performed under the following conditions, by filling a sample holder portion of a non-reflective silicon sample plate for X-ray diffraction with a ground crystal sample.

Powder X-ray diffraction measurement apparatus: RINT2000 (manufactured by Rigaku Corporation)

X-ray type: Cu-Kα radiation (λ=1.54 Å)

Diffraction angle 2θ scanning range: 2.000 to 40.000°

Sampling width: 0.020°

Scanning rate: 2.000°/min

FIG. 1 shows the obtained diffraction pattern. In FIG. 1, the vertical axis represents a diffraction intensity (count/sec (cps)), and the horizontal axis represents a diffraction angle 2θ)(°).

For main peaks with an intensity of more than 1,700 cps, the diffraction angle 2θ, full width at half maximum, d-value, intensity and relative intensity are shown in Table 6.

TABLE 3

| Peak number | 2θ | Full width at half maximum | d-value | Intensity | Relative intensity |
|---|---|---|---|---|---|
| 1 | 7.260 | 0.282 | 12.166 | 1,718 | 35 |
| 2 | 14.580 | 0.306 | 6.070 | 2,785 | 56 |
| 3 | 15.340 | 0.306 | 5.771 | 5,016 | 100 |
| 4 | 16.240 | 0.400 | 5.453 | 2,170 | 44 |
| 5 | 18.180 | 0.494 | 4.876 | 1,785 | 36 |
| 6 | 18.900 | 0.306 | 4.691 | 2,175 | 44 |
| 7 | 20.640 | 0.329 | 4.300 | 2,696 | 54 |
| 8 | 21.480 | 0.235 | 4.133 | 1,758 | 36 |
| 9 | 22.480 | 0.494 | 3.952 | 4,036 | 81 |
| 10 | 24.140 | 0.259 | 3.684 | 1,855 | 37 |

FIG. 1 and Table 3 reveal that main peaks are present at diffraction angles (2θ) of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2°.

In addition, it is revealed that peaks with a high intensity are present at diffraction angles (2θ) of around 14.6±0.2°, around 15.3±0.2°, around 20.6±0.2° and around 22.5±0.2°, particularly around 15.3±0.2° and around 22.5±0.2°.

The above measurement results show that the pemafibrate crystal has a peak at one or more diffraction angles (2θ) selected from the group consisting of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2°.

<Melting Point Measurement>

Using a precise melting point measuring instrument (MEL-270 manufactured by SIBATA SCIENTIFIC TECHNOLOGY LTD.), the melting point was measured in accordance with The Japanese Pharmacopoeia, 17th Edition, Melting Point Determination Method 1.

The melting point measurement was conducted three times. The average value thereof was 99.5° C.

The above measurement results show that when measured in accordance with The Japanese Pharmacopoeia, 17th Edition, Melting Point Determination Method 1, the melting point of the pemafibrate crystal is 95 to 101° C., particularly preferably 97 to 100° C.

<Hygroscopic Property Evaluation>

250 mg of the pemafibrate crystal was placed in a dish, and stored in an uncapped state (open state) in a dark place at 25° C. and 83% relative humidity (RH) for 3 months. The hygroscopic property was evaluated by measuring the moisture contents before and after the storage. The measurement of the moisture content was performed by a coulometric titration method in accordance with The Japanese Pharmacopoeia, 17th Edition, Moisture Content Measurement Method (Karl Fischer Method).

Table 4 shows the results.

TABLE 4

| | Moisture content (%) | |
|---|---|---|
| | Before storage | After storage at 25° C. and 83% RH for 3 months |
| Pemafibrate crystal Stored in dish in open state | <0.1 | <0.1 |

Table 4 reveals that the moisture content of the pemafibrate crystal was not substantially changed even after storage at a high humidity of 83% RH for a long period of time, and thus the pemafibrate crystal was not hygroscopic. Therefore, it is revealed that a pharmaceutical composition containing the pemafibrate crystal is readily adjusted in terms of moisture content at the time of production and the change of moisture content during storage can be suppressed.

Production Examples 1 to 6

Tablets containing the components in the amounts (mg) thereof per tablet shown in Table 5 are conventionally produced. The "Moisture content (loss-on-drying value) (mass %)" in the table is a loss-on-drying value obtained when a test is conducted in accordance with The Japanese Pharmacopoeia, 17th Edition, Loss-on-Drying Test Method.

TABLE 5

| | Amount blended (mg) (per tablet) | | | | | |
|---|---|---|---|---|---|---|
| Components | Production Example 1 | Production Example 2 | Production Example 3 | Production Example 4 | Production Example 5 | Production Example 6 |
| Pemafibrate | 0.1 | 0.2 | 0.4 | 0.1 | 0.2 | 0.4 |
| Lactose monohydrate | q.s. | q.s. | q.s. | q.s. | q.s. | q.s. |
| Microcrystalline cellulose | 20 | 20 | 20 | 20 | 20 | 20 |
| Croscarmellose sodium | 2 | 2 | 2 | 2 | 2 | 2 |
| Magnesium stearate | 1 | 1 | 1 | 1 | 1 | 1 |
| Total | 100 | 100 | 100 | 100 | 100 | 100 |
| Moisture content (loss-on-drying value) (mass %) | 0.3% | 0.5% | 1.0% | 1.7% | 1.9% | 2.1% |

Production Examples 7 to 12

The tablets of Production Examples 1 to 6 are stored in high-density polyethylene bottles to obtain pharmaceutical preparations of Production Examples 7 to 12, respectively.

Production Examples 13 to 18

The tablets of Production Examples 1 to 6 are placed in pocket portions formed on a resin sheet (SUMILITE VSS-1202 (trade name) manufactured by Sumitomo Bakelite Co., Ltd.) beforehand, the pockets are then capped with PTP aluminum foil (Aluminum Foil Silver Base (trade name) manufactured by Daiwa Chemical Industries Co., Ltd.) to pack the tablets in a PTP package. 3 sheets of the obtained PTP package (each sheet contains 10 tablets) are further packed in an aluminum pillow package. Accordingly, pharmaceutical preparations of Production Examples 13 to 18, respectively, can be obtained.

Production Examples 19 to 24

The tablets of Production Examples 1 to 6 are placed in pocket portions formed on a resin sheet (SUMILITE VSS-1104 (trade name) manufactured by Sumitomo Bakelite Co., Ltd.) beforehand, the pockets are then capped with PTP aluminum foil (Aluminum Foil Silver Base (trade name) manufactured by Daiwa Chemical Industries Co., Ltd.) to pack the tablets in a PTP package. 2 sheets of the obtained PTP package (each sheet contains 12 tablets) are packed in an aluminum pillow package. Accordingly, pharmaceutical preparations of Production Examples 19 to 24, respectively, can be obtained.

Production Examples 25 to 30

The tablets of Production Examples 1 to 6 are placed in pocket portions formed on a resin sheet (SUMILITE VSL-4501 (trade name) manufactured by Sumitomo Bakelite Co., Ltd.) beforehand, the pockets are then capped with PTP aluminum foil (Aluminum Foil Silver Base (trade name) manufactured by Daiwa Chemical Industries Co., Ltd.) to pack the tablets in a PTP package. 3 sheets of the obtained PTP package (each sheet contains 10 tablets) are further packed in an aluminum pillow package. Accordingly, pharmaceutical preparations of Production Examples 25 to 30, respectively, can be obtained.

Production Examples 31 to 36

The tablets of Production Examples 1 to 6 are stored in glass bottles to obtain pharmaceutical preparations of Production Examples 31 to 36, respectively.

INDUSTRIAL APPLICABILITY

The present invention enables provision of a pharmaceutical composition having excellent stability and containing pemafibrate which exhibits plasma triglyceride concentration reducing action, HDL cholesterol increasing action, etc. The pharmaceutical composition can be used in, for example, pharmaceutical preparation industries.

The invention claimed is:

1. A pharmaceutical composition comprising pemafibrate, a salt thereof or a solvate thereof and having a moisture content of 0.3 to 2.4 mass %.

2. The pharmaceutical composition according to claim 1, wherein the moisture content is 0.8 to 1.5 mass %.

3. The pharmaceutical composition according to claim 1, wherein the pharmaceutical composition is a solid preparation.

4. The pharmaceutical composition according to claim 1, wherein the pharmaceutical composition is a tablet, a capsule, a granule, a powder or a pill.

5. A pharmaceutical preparation obtained by storing the pharmaceutical composition according to claim 1 in a tight package.

6. A pharmaceutical preparation according to claim 5, wherein the tight package is one or more selected from the group consisting of a bottle package, an SP package, a PTP package, a pillow package and a stick package.

7. A method for stabilizing pemafibrate, a salt thereof or a solvate thereof in a pharmaceutical composition, the method comprising setting a moisture content in a pharmaceutical composition comprising pemafibrate, a salt thereof or a solvate thereof 0.3 to 2.4 mass %.

8. A pharmaceutical composition comprising a pemafibrate crystal having a moisture content of 0.3 to 2.4 mass %.

9. The pharmaceutical composition according to claim 8, wherein the pemafibrate crystal has a peak at one or more diffraction angles (2θ) selected from the group consisting of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

10. The pharmaceutical composition according to claim 9, wherein the pemafibrate crystal has peaks at diffraction angles (2θ) of around 14.6±0.2°, around 15.3±0.2°, around 20.6±0.2° and around 22.5±0.2° in a powder X-ray diffraction pattern obtained by irradiation with Cu-Kα radiation.

11. The pharmaceutical composition according to claim 9, wherein the pemafibrate crystal has peaks at diffraction angles (2θ) of around 7.3±0.2°, around 14.6±0.2°, around 15.3±0.2°, around 16.2±0.2°, around 18.2±0.2°, around 18.9±0.2°, around 20.6±0.2°, around 21.5±0.2°, around 22.5±0.2° and around 24.1±0.2° in a powder X-ray diffraction pattern obtained by irradiation with Cu-Kα radiation.

12. The pharmaceutical composition according to claim 8, wherein the pemafibrate crystal is a crystal having a melting point of 95 to 101° C.

13. The pharmaceutical composition according to claim 8, wherein the moisture content of the pharmaceutical composition is 0.5 to 2.1 mass %.

14. The pharmaceutical composition according to claim 8, wherein the moisture content of the pharmaceutical composition is 0.8 to 1.9 mass %.

15. The pharmaceutical composition according to claim 8, wherein the moisture content of the pharmaceutical composition is 1.0 to 1.7 mass %.

16. The pharmaceutical composition according to claim 8, wherein the moisture content of the pharmaceutical composition is 1.2 to 1.5 mass %.

17. The pharmaceutical composition according to claim 8, wherein the pharmaceutical composition is a solid preparation.

18. The pharmaceutical composition according to claim 17, wherein the pharmaceutical composition is a tablet, a capsule, a granule, a powder or a pill.

19. The pharmaceutical composition according to claim 8, wherein the pharmaceutical composition is an agent for prevention and/or treatment of a disease selected from dyslipidemia, NAFLD and primary biliary cirrhosis.

20. A pharmaceutical preparation obtained by storing the pharmaceutical composition according to claim 8 in a tight package.

21. The pharmaceutical preparation according to claim 20, wherein the tight package is one or more selected from the group consisting of a bottle package, an SP package, a PTP package, a pillow package and a stick package.

* * * * *